United States Patent [19]

Jaxa-Chamiec et al.

[11] Patent Number: 5,441,731
[45] Date of Patent: Aug. 15, 1995

US005441731A

[54] COMPOUNDS

[75] Inventors: Albert A. Jaxa-Chamiec, Rickmansworth; Deirdre M. B. Hickey, Sawston; David Alston, Hull, all of England

[73] Assignee: SmithKline & French Laboratories Ltd., Hertfordshire, England

[21] Appl. No.: 837,793

[22] Filed: Feb. 18, 1992

Related U.S. Application Data

[63] Continuation of Ser. No. 449,013, Dec. 11, 1989, abandoned.

[30] Foreign Application Priority Data

Dec. 13, 1988 [GB] United Kingdom ............... 8829088

[51] Int. Cl.$^6$ .................................................. A61K 31/74
[52] U.S. Cl. ..................................... 424/78.1; 424/78.37
[58] Field of Search ............... 424/78.1, 78.37, 78.27, 424/784, 78.57; 526/307, 307.1, 307.2, 307.3; 525/329.9, 330.5, 379

[56] References Cited

U.S. PATENT DOCUMENTS

| | | | |
|---|---|---|---|
| 2,843,573 | 7/1958 | Melamed | 526/307 |
| 4,139,684 | 2/1979 | Coupek et al. | 526/307 |
| 4,981,936 | 1/1991 | Good, Jr. et al. | 526/307 |

FOREIGN PATENT DOCUMENTS

| | | | |
|---|---|---|---|
| 756035 | 11/1971 | Belgium . | |
| 50-110482 | 8/1975 | Japan | 521/38 |

*Primary Examiner*—Thurman K. Page
*Assistant Examiner*—Peter F. Kulkosky
*Attorney, Agent, or Firm*—Wayne J. Dustman; Stephen Venetianer; Edward T. Lentz

[57] ABSTRACT

Polymethacrylate polymers, pharmaceutical compositions containing them and their use in medicine as cholesterol lowering agents. A particular polymer of the invention is 11-N,N,N-trimethylammonioundecyl methacrylate chloride copolymer.

21 Claims, No Drawings

COMPOUNDS

This is a Continuation of application Ser. No. 07/449,013 filed Dec. 11, 1989, now abandoned.

The present invention relates to novel anion exchange polymers, processes for their preparation, pharmaceutical compositions containing them and their use in the lowering of plasma cholesterol levels in mammals, in particular humans.

Coronary Heart Disease (CHD) is one of the most serious health problems of contemporary society. Worldwide epidemiological studies have shown that the incidence of CHD is related to a number of independent risk factors, in particular, for example, high concentrations of serum cholesterol (hypercholesterolaemia). Such adverse factors lead to atherosclerosis, and ultimately, in severe cases, intermittent claudication, cerebrovascular insufficiency, thrombosis and cardiac arrest.

It is known that ion exchange polymers can be used as sequestering agents to bind bile acids and salts in the intestinal tract, forming complexes which are then excreted in the faeces. This sequestering leads to a decrease in the amount of bile acids returning to the liver via enterohepatic circulation. The synthesis of replacement bile acids from hepatic cholesterol depletes hepatic cholesterol, regulates hepatic LDL receptors and consequently reduces plasma cholesterol levels. Such sequestering polymers have been recognised as useful for the treatment of hypercholesterolaemia and it is now proven that reducing serum cholesterol with bile acid sequestrants has a beneficial effect on protecting against the occurrence of coronary heart disease.

One particular agent which is currently used to lower serum cholesterol levels in humans by binding bile acids in the intestinal tract is cholestyramine. Cholestyramine is a cross-linked anion exchange polystyrene polymer bearing an ionisable trimethylammonium group bound to the polymer backbone. However, the use of this agent is associated with a number of undesirable side-effects, for example, it is unpalatable and must be taken in high doses and causes, in some cases, bloating, constipation and other gut side-effects. Furthermore, its ability to bind bile acids is inefficient with respect to the amounts of resin which it is necessary to use (up to 36 g per person per day).

In addition, other polymers have been disclosed in the art as sequestering agents, in particular U.S. Pat. No 3,787,474 discloses the use of polymers derived from acrylic monomers of structure RCH=CHR$^1$A in which R is methyl or ethyl, R$^1$ is hydrogen or methyl and A is for example CO$_2$(CH$_2$)$_2$N(R$^3$)$_2$R$^4$X in which R$^3$ is methyl or ethyl, and R$^4$ is hydrogen, methyl or ethyl and X is Cl$^-$, Br$^-$, I$^-$ or CH$_3$SO$_3-$, cross-linked with methyl bisacrylamide or ethylene glycol bis methacrylate; U.S. Pat. No. 4,393,145 discloses further polymers derived from acrylic monomers cross-linked through divinyl benzene (10 to 12%), and SE 7906129 discloses acrylic polymers cross-linked by 10–12% of a divinyl cross-linking monomer. However, despite these disclosures, no such acrylic polymers are available for human use and there remains a need for effective bile acid sequestering agents which do not have the disadvantages associated with agents currently in use.

The present invention therefore provides in a first aspect, cross-linked polymers of structure (I)

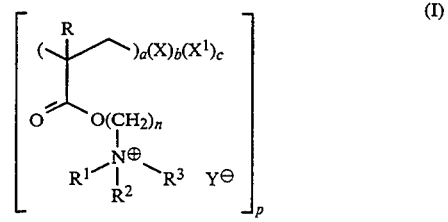

in which
a, b and c indicate the relative molar percentages of the units present in the polymer, (a) being from about 25 to about 99.5 molar percent, and (b) being from about 0.5 to about 8 molar percent;
X is a cross-linking unit;
X$^1$ is a comonomer unit;
R is hydrogen or C$_{1-4}$alkyl;
R$^1$ and R$^2$ are the same or different and are each C$_{1-4}$alkyl, and R$^3$ is C$_{1-20}$alkyl or C$_{1-20}$aralkyl; or R$^1$ is C$_{1-4}$alkyl and R$^2$ and R$^3$ together with the nitrogen atom to which they are attached form a saturated ring, optionally containing one or more further heteroatoms; or R$^1$ to R$^3$ together with the nitrogen atom to which they are attached form an unsaturated ring, optionally containing one or more further heteroatoms;
n is 1 to 20;
p is a number indicating the degree of polymerisation of the polymer; and
Y$^-$ is a physiologically acceptable counter ion, provided that,
   (i) when n is 1 to 5 R$^1$ R$^2$ and R$^3$ are not all C$_{1-4}$alkyl; and
   (ii) when n is 1 to 5, R$^1$, R$^2$ and R$^3$ do not together form an unsaturated ring.

Suitably, (a) is from about 25 to about 99.5 molar percent; preferably from about 60 to about 99.5 molar percent.

Suitably, (b) is from about 0.5 to about 8 molar percent; preferably from about 0.5 to about 5.0 molar percent.

Suitably, X is a cross-linking unit i.e. a unit which provides a random distribution of cross-links between chains of polymers.

Preferred such units include, for example, divinylbenzene, alkylene glycol bis methacrylates of structure (i)

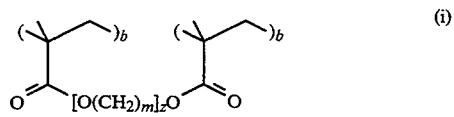

in which m is 2 to 6, z is 1 to 4 and (b) comprises from about 0.5 to about 8 molar percent of said polymer; and trismethacrylates of structure (ii)

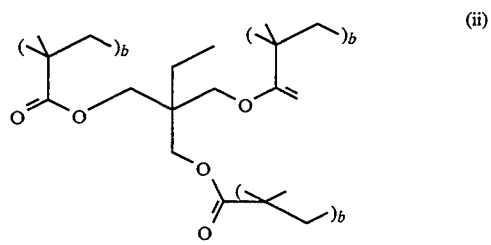

Suitably, z is 1 to 4, preferably z is 1. Suitably, m is 2 to 6, preferably m is 2.

Suitably $X^1$ is a comonomer unit. Preferably $X^1$ is styrene, an alkyl alkylate of structure (ii) or an alkylstyrene of structure (iii)

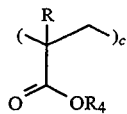
(ii)

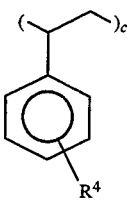
(iii)

in which R and c are as described for structure (I) and $R^4$ is $C_{1-20}$alkyl. In such comonomers groups R is preferably methyl and $R^4$ is preferably $C_{6-12}$alkyl.

Suitably $R^1$ to $R^3$ together with the nitrogen atom to which they are attached form an unsaturated ring optionally containing one or more further heteroatoms. Suitable examples of such rings unsaturated 5 or 6 membered rings such as imidazolyl and pyridyl. More suitably, $R^1$ is $C_{1-4}$alkyl and $R^2$ and $R^3$ together with the nitrogen atom to which they are attached form a saturated ring optionally containing one or more further heteroatoms. Suitable examples of saturated rings include, for example, morpholino, piperidino and piperazino rings, and in addition, bicyclic rings i.e. those in which the $R^1$ group forms a bridge between the two nitrogen atoms of a saturated ring e.g. diazabicyclo [2.2.2] octane rings of structure

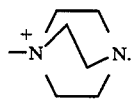

Preferably, $R^1$ and $R^2$ are the same or different and are each $C_{1-4}$alkyl; more preferably $R^1$ and $R^2$ are the same and are each $C_{1-4}$alkyl, in particular methyl; and $R^3$ is $C_{1-20}$alkyl or $C_{1-20}$aralkyl, preferably $C_{1-20}$alkyl, most preferably $C_{1-12}$alkyl, in particular $C_{12}$alkyl.

Suitably, n is 1 to 20; preferably n is 10 to 20; most preferably n is 10 to 12.

p is a number indicating the degree of polymerisation of the polymer. Owing to the three dimensional crosslinkage, precise figures cannot be given for p, but in any case will be greater than 1,000.

Suitably $Y^-$ is a physiologically acceptable counter ion such as a bicarbonate, carbonate, formate, acetate, sulphonate, propionate, malonate, succinate, maleate, tartrate, citrate, maleate, fumarate, ascorbate, sulphate, phosphate, halide or glucuronate; or the anion of an amino acid such as aspartic or glutamic acid. Preferably $Y^-$ is a sulphate, phosphate or halide ion; more preferably a halide ion, in particular a chloride ion.

It is to be noted that $C_{1-4}$alkyl and $C_{1-20}$alkyl groups as herein defined include both straight and branched alkyl groups.

A preferred sub-class of polymers falling within the present invention is the polymers of structure (IA)

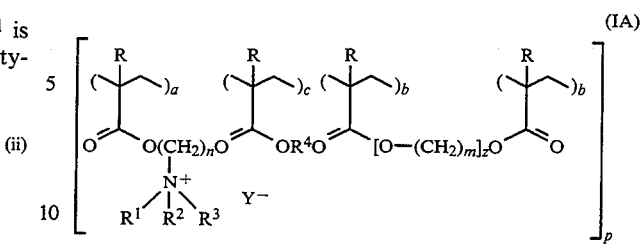
(IA)

in which (a), (b) and (c) indicate the relative molar percentages of the units present in the polymer, (a) being from about 25 to about 99.5 molar percent and (b) being from about 0.5 to about 8 molar percent;

R is $C_{1-4}$alkyl;

$R^1$ and $R^2$ are each $C_{1-4}$alkyl;

$R^3$ is $C_{1-20}$alkyl or $C_{1-20}$aralkyl, or $R^1$ and $R^2$ are the same or different and are each $C_{1-4}$alkyl, and $R^3$ is $C_{1-20}$alkyl or $C_{1-20}$aralkyl; or $R^1$ is $C_{1-4}$alkyl and $R^2$ and $R^3$ together with the nitrogen atom to which they are attached form a saturated ring, optionally containing one or more further heteroatoms; or $R^1$ to $R^3$ together with the nitrogen atom to which they are attached form an unsaturated ring, optionally containing one or more further heteroatoms;

n is 1 to 20; and $R^4$ is $C_{1-20}$alkyl;

m is 2 to 6;

z is 1 to 4;

$Y^-$ is a physiologically acceptable counter ion; and p is a number indicating the degree of polymerisation of said polymer;

provided that, (i) when n is 1 to 5, $R^1$, $R^2$ and $R^3$ are not all $C_{1-4}$alkyl; and (ii) when n is 1 to 5, $R^1$, $R^2$ and $R^3$ do not together form an unsaturated ring.

The polymers of the present invention are also characterised by their total exchange capacity i.e. the theoretical maximum capacity of the resin if each counter ion were to be exchanged with bile acid. In this specification the total exchange capacity is defined in terms of the number of milliequivalents of counter ion per gram of dry weight of polymer.

Suitable total exchange capacities are in the range of, for example where the counter ion $Y^-$ is chlorine, from about 1.5 to about 5.0 meq $Cl^-$ per gram of resin. Preferred within this range are polymers having a total exchange capacity of between 2 and 3 meq $Cl^-$/gram of resin.

It is to be noted that the term 'bile acid' when used herein shall be taken to include bile acids, bile salts and conjugates thereof.

The polymers of the present invention can be prepared by processes analogous to those known in the art. The present invention therefore provides, in a further aspect, a process for preparing the polymers of structure (I) which comprises:

(a) reaction of a polymer of structure (II)

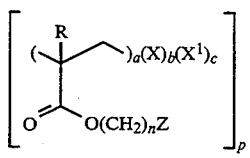

(II)

in which a, b, c, p, R, X, $X^1$ and n, are as described for structure (I), and Z is a group displaceable by an amine, with a compound of structure $R^1R^2R^3N$, in which $R^1$ to $R^3$ are as described for structure (I); or (b) reaction of a polymer of structure (III)

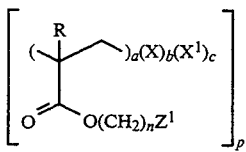

(III)

in which a, b, c, p, R, X, $X^1$ and n are as described for structure (I), and $Z^1$ is a group $NR^1R^3$ or $NR^1R^2$ in which $R^1$ to $R^3$ are as described for structure (I) with a compound of structure $R^5Z$ in which $R^5$ is a $C_{1-4}$alkyl group when $Z^1$ is $NR^1R^3$ or a $C_{1-20}$alkyl or $C_{1-20}$aralkyl group when $Z^1$ is $NR^1R^2$ and Z is a group displaceable by an amine; or (c) reaction of a polymer of structure (IV)

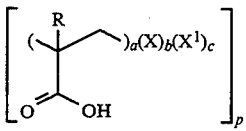

(IV)

in which a, b, c, p and R are as described for structure (I), with a compound of structure $Z^2(CH_2)_n{}^+NR^1R^2R^3M^-$(V) in which n, $R^1$, $R^2$ and $R^3$ are as described for structure (I), $M^-$ is a counter ion and $Z^2$ is a leaving group displaceable by a carboxylate anion.

Suitable groups Z displaceable by an amine will be apparent to those skilled in the art and include for example halogen, such as bromine.

Suitable leaving group $Z^2$ displaceable by a carboxylate anion will be apparent to those skilled in the art and include for example, halogen, preferably bromine, and sulphonic acids such as p-toluene sulphonic or methane sulphonic acid.

Suitable counter ions $M^-$ are, for example, as described herein for $Y^-$.

The reaction between a polymer of structure (II) and a compound of structure $R^1R^2R^3N$ can be carried out in a suitable solvent at elevated temperature. Suitable solvents included for example, a $C_{1-4}$alkanol such as methanol, N-methylpyrrolidone, dimethylformamide, tetrahydrofuran, nitromethane or sulpholane. Preferably the reaction is carried out in methanol at a temperature of about 40° for a period of up to 24 hours or until the reaction is complete.

The reaction between a polymer of structure (III) and a compound of $R^5Z$ can be carried out in a suitable inert solvent such as a $C_{1-4}$alkanol, dimethylformamide, N-methylpyrrolidone or tetrahydrofuran at elevated temperature.

The reaction between a polymer of structure (IV) and a compound of structure (V) can be carried out in a suitable solvent at a temperature of between ambient and the reflux temperature of the solvent used.

The intermediate polymers of structure (II) can be prepared from readily available materials by methods known to those skilled in the art. For example polymers of structure (II) in which X is a cross-link of structure (i) in which z is 1 and m is 2, and Z is bromine and R is methyl can be prepared by reaction of the appropriate bromo alkyl methacrylate, ethylene glycol bis methacrylate, and, optionally, for example, a $C_{1-20}$alkyl alkacrylate (if a comonomer unit $X^1$ is desired in the final polymer) in an aqueous suspension comprising polyvinyl alcohol in the presence of an initiator at elevated temperature. Suitable initiators will be apparent to those skilled in the art and include, for example azobisisobutyronitrile benzoyl peroxide and WAKO V601 (Trade name-$MeO_2C(CH_3)CN=NC(CH_3)_2CO_2Me$).

The intermediate polymers of structure (III) can be prepared from the polymers of structure (II) by reaction with an amine of structure $R^1R^2NH$ or $R^1R^3NH$ under the same or similar conditions as indicated for the reaction of a compound of structure (II) and a compound of structure $R^1R^2R^3N$.

The intermediate polymers of structure (III) can also be prepared by copolymerising a monomer of structure (VII)

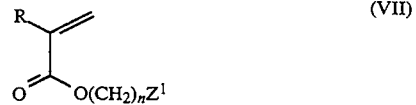

(VII)

in which R, n, and $Z^1$ are as defined for structure (III) with a suitable cross-linking agent (X) and optionally a comonomer unit ($X^1$) in an aqueous suspension comprising polyvinyl alcohol in the presence of an initiator at elevated temperature.

The intermediates of structure (IV) are available commercially or can be prepared by standard techniques.

The starting monomers can be prepared by methods apparent to those skilled in the art. For example, chloro or bromo alkyl methacrylates can be prepared by reaction of the corresponding chloro- or bromoalkanol and methacrylic anhydride in the presence of 4-dimethylaminopyridine (DMAP) in a suitable solvent such as pyridine, or by reaction of the corresponding chloro or bromo alkanol with methacryloyl chloride in the presence of a base in a suitable solvent—suitable combinations of bases and solvents include, for example sodium bicarbonate in petroleum spirit as a solvent and pyridine as a base in toluene as solvent (cf. method described in Polymer (1987), 28, 325–331, and Br. Polymer J. (1984) 16, 39–45).

Alternatively, the starting bromoalkyl methacrylate monomers can be prepared by transesterification of methyl methacrylate in the presence of a suitable catalyst and stabiliser. This finding is surprising since it has been found that a range of catalysts known in the art to be useful in transesterification reactions e.g. boron trifluride, zinc chloride and sodium methoxide, are not effective in reactions of this type. However, the transesterification of methyl methacrylate with, for example 11-bromoundecanol can be successfully carried out, in high yield, using a titanium tetra$C_{1-4}$alkoxide catalyst in the presence of a suitable stabiliser. Particular catalysts include titanium tetramethoxide and titanium tetraisopropoxide, and particular stabilisers include 2,6-di-t-butyl-4-methylphenol (BHT), butylated hydroxyanisole and phenothiazine. Preferably, titanium tetraisopropoxide in the presence of BHT is used to carry out the reaction.

The present invention therefore provides, in a further aspect a process for preparing a compound of structure

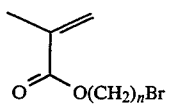

in which n is 1 to 20, which comprises transesterification of methyl methacrylate, with a bromoalkanol of structure $HO(CH_2)_nBr$ in which n is 1 to 20, in the presence of a titanium tetra$C_{1-4}$alkoxide catalyst and a stabiliser.

The polymers of structure (I) have been found to bind bile acids both in in vitro and in in vivo models. As indicated earlier it is recognised that removal of bile acids from the intestinal tract in this way lowers serum cholesterol levels and also has a beneficial effect on protecting against atherosclerosis and its dependent clinical conditions. The present invention therefore provides in a further aspect, a method for the lowering of serum cholesterol levels in mammals, including humans which comprises administering to a subject in need thereof an effective amount of a polymer of structure (I). In addition the polymers of structure (I) are expected to be of use in the treatment of atherosclerosis and its sequelae, and for example, in the treatment of pruritus and diarrhoea.

When used in the methods of the invention the polymers of structure (I) are in general administered in a pharmaceutical composition.

In a still further aspect of the present invention there is therefore provided a pharmaceutical composition comprising a polymer of structure (I) in association with a pharmaceutically acceptable carrier.

The compositions of the present invention can be prepared by techniques well known to those skilled in the art of pharmacy.

The polymers are preferably administered as formulations in admixture with one or more conventional pharmaceutical excipients which are physically and chemically compatible with the polymer, which are non-toxic, are without deleterious side-effects but which confer appropriate properties on the dosage form.

In general, for liquid formulations, aqueous pharmaceutically acceptable carriers such as water itself or aqueous dilute ethanol, propylene glycol, polyethylene glycol or glycerol or sorbitol solutions are preferred. Such formulations can also include preservatives and flavouring and sweetening agents such as sucrose, fructose, invert sugar, cocoa, citric acid, ascorbic acid, fruit juices etc. In general, digestible oil or fat based carriers should be avoided or minimised as they contribute to the condition sought to be alleviated by use of the polymers. They are also subject to absorption by the polymers during prolonged contact, thus reducing the capacity of the polymer to absorb bile acids after administration.

The polymers can also be prepared as 'concentrates', for dilution prior to administration, and as formulations suitable for direct oral administration. They can be administered orally ad libitum, on a relatively continuous basis for example by dispersing the polymer in water, drinks or food, for example in a granule presentation suitable for admixture with water or other drink to provide a palatable drinking suspension.

Preferably, the polymers are administered in tablet form or in gelatin capsules containing solid particulate polymer or a non-aqueous suspension of solid polymer containing a suitable suspending agent. Suitable excipients for such formulations will be apparent to those skilled in the art and include, for example, for tablets and capsules, lactose, microcrystalline cellulose, magnesium, stearate, povidone, sodium starch, glycollate and starches; and for suspensions in capsules, polyethylene glycol, propylene glycol and colloidal silicone dioxide. If desired these dosage forms in addition optionally comprise suitable flavouring agents. Alternatively, a chewable tablet or granule presentation incorporating suitable flavouring and similar agents may be used.

Preferably the polymer is administered in unit dosage form, each dosage unit containing preferably from 0.5 g to 1.5 g of polymer.

The daily dosage regimen for an adult patient may be, for example, a total daily oral dose of between 1 and 10 g, preferably 1–5 g, the compound being administered 1 to 4 times a day. Suitably the compound is administered for a period of continuous therapy of one month or more sufficient to achieve the required reduction in serum cholesterol levels.

In addition the polymers of the present invention can be co-administered (together or sequentially) with further active ingredients such as HMGCoA reductase inhibitors and other hypocholesterolaemic agents, and other drugs for the treatment of cardiovascular diseases.

The following data and examples indicate the properties and preparation of the polymers of the present invention. Temperatures are recorded in degrees celsius. The exchange capacity of the ammonium substituted polymers was determined by elemental analysis and/or potentiometric titration of chloride ion. Figures quoted are expressed as milli equivalents of exchangeable chloride ion per gram of dry resin weight; and the percent cross-linking values given are based on the ratios of the starting monomers used in the polymerisation stage.

EXAMPLE 1

Preparation of 11-bromoundecanol 11-bromoundecanol can be prepared using either of the following methods (i) Sodium Borohydride (28.8 g, 0.76 mole) was dissolved in diglyme (700 ml) and THF (300 ml) and the solution cooled to 20° (dissolution of the NaBH$_4$ is slightly exothermic). BF$^3$OEt$_2$ (145 g, 1.02 mole) was then added dropwise, with external cooling, at such a rate to keep the temperature of the mixture below 15°. After the addition was complete the mixture was stirred for 0.5 hour at 10°. This reducing agent was then added slowly to a solution of 11-bromoundecanoic acid (200 g, 0.76 mole) in THF (400 ml) keeping the temperature below 20°. After the addition was complete, the reaction was stirred at room temperature for 1.5 hours then quenched by pouring onto water (3 L) and concentrated HCl (100 ml). The quenched mixture was stirred for 0.5 hour at room temperature then cooled to 5°. The crystalline product was filtered off, washed with water (3×1 L) and dried under vacuum to give 11-bromoundecanol (189.2 g, 99.2%).

(2) Sodium Borohydride (16.32 g, 0.43 mole) was dissolved in diglyme (350 ml). To this was added a solution of aluminium trichloride (19.2 g, 0.14 mole) in diglyme (250 ml) maintaining the temperature below 20°. After the addition was complete, the mixture was stirred for 0.5 hour at room temperature. The reducing agent was then added dropwise to a solution of methyl 11-bromoundecanoate* (120 g, 0.43 mole) in diglyme (200 ml) maintaining the temperature at 10°. After the addition was complete the reaction was stirred at 20° for 3 hours and then quenched by pouring onto water (2 L) and concentrated HCl (100 ml). The quenched mixture was stirred for 1 hour then cooled to 15°. The product was filtered off, washed with water (2×500 ml) and dried under vacuum to give 11-bromoundecanol (106.8 g, 98.9%).

* This methyl ester can be produced in quantitative yield by esterifying 11-bromoundecanoic acid with MeOH/$H_2SO_4$ (a) A suspension of 11-bromoundecanol (100 g) and 4-dimethylaminopyridine (DMAP) (1 g) in methacrylic anhydride (60 ml) and pyridine (37 ml) was stirred for 48 hours at room temperature. Water (400 ml) was added and the aqueous phase brought to pH 3 using dilute hydrochloric acid. The aqueous phase was extracted with hexane (3×300 ml). The combined organic extracts were washed with 2M HCl (200 ml), water (200 ml), saturated sodium hydrogen carbonate solution (2×400 ml) and finally water (200 ml). After drying ($MgSO_4$), the solution was concentrated in vacuo to give a clear oil (108 g). This was subjected to column chromatography on silica gel with hexane as eluent, to give 11-bromoundecyl methacrylate as a clear oil (70.8 g, 56% yield).

Alternatively, the 11-bromoundecyl methacrylate can be prepared by transesterification, as follows:

Methyl methacrylate (1.15 L, stabilised with 50 ppm of BHT), 11-bromoundecanol (200 g, 0.8 mole) and titanium tetraisopropoxide (11.4 g, 0.04 mole) are mixed together. A constant slow stream of dry air is bubbled through the reaction mixture during the reaction. The reaction mixture is heated under gentle reflux for 1 hour (internal temperature 90°). After this reflux period the methyl methacrylate/methanol azeotrope is removed under atmospheric distillation. During this time the internal temperature rises to 104° and the temperature at the still head rises from 65° to 101° (a total of 550 ml of distillate is collected). The reaction mixture is then cooled to 40° and quenched with water (1.5 ml, 2 equiv. based on titanium tetraisopropoxide). The resulting mixture is stirred for 3 hours then treated with celite (20 g). After stirring for a further 10 minutes the reaction mixture is filtered through a pad of celite. The filter pad is washed with methyl methacrylate (50 ml). The filtrate and wash are combined and distilled under vacuum (4–10 mmHg) at room temperature, then at 50°–60° to remove last traces of methyl methacrylate. During distillation a slow stream of dry air is bubbled through the residue in the distillation vessel. The product, 11-bromoundecyl methacrylate (233 g, 91% yield) is obtained as a pale yellow oil.

(b) 11-Bromoundecyl methacrylate (49.5 g), ethylene glycol bismethacrylate (0.5 g) and azo-bis-isobutyronitrile (AIBN) (0.5 g) were mixed to give a suspension and added to a solution of poly(vinyl alcohol) (m.w. 125,000) (1.0 g) in distilled water (500 ml). The mixture was then stirred at 80° under an atmosphere of nitrogen at such a rate as to maintain the monomers in suspension. After 7 hours the stirring was stopped and the mixture poured into distilled water. The resin formed was washed by decantation with cold and hot water, filtered, and washed with acetone and ether. Drying under reduced pressure gave an approximately 1.6 molar % cross-linked 11-bromoundecyl methacrylate co-polymer containing 3.1 meq Br/g (24.7 g).

Alternatively, the 11-bromoundecyl methacrylate copolymer was prepared as follows:

Polyvinyl alcohol (173.3 g) was dissolved in distilled water (3.33 L) and the resultant solution was filtered into a reactor containing 130 kg of filtered, demineralised water.

A mixture of 11-bromoundecylmethacrylate (13.2 kg) and ethylene glycol bismethacrylate (133.3 g) was treated with azo-bis-isobutyronitrile (or azo-bizmethylisobutyrate) (133.3 g). The resulting solution was filtered into the reactor. The reactor contents were heated with stirring to 80° and kept at this temperature for 7 hours. The reaction mixture was cooled and the beads were allowed to settle. The supernatant was decanted, and the residue washed with filtered demineralised water (100 L) with stirring. The beads were allowed to settle and the supernatant was decanted. This process was repeated until the washings were clear, usually three washes were necessary. The residual beads were washed with filtered methanol (50 L) twice, decanting the methanol in between washes as before. The residual methanol/polymer slurry was then used in the subsequent quarternisation step. Weight of slurry 23.55 kg estimated at 47.0% solids (76% of theory).

(c) The above 1.6 molar % cross-linked 11-bromoundecyl methacrylate co-polymer (5.3 g) was suspended in dimethylformamide (40 ml), 33% trimethylamine in ethanol (20 ml) added, and the reaction mixture heated at 70° for 40 hours. Additional 33% trimethylamine in ethanol was added (20 ml) at 16 and 24 hours. The polymer was filtered and washed with dimethylformamide and methanol. Anion-exchange was accomplished by stirring the polymer in 2M HCl (500 ml) for 16 hours. It was then filtered and washed with 2M HCl, water, methanol and ether and finally dried under vacuum to give cross-linked 11-N,N,N-trimethylammoniundecyl methacrylate chloride co-polymer beads (4.93 g), (exchange capacity=2.76 meq $Cl^-/g$).

Alternatively, the 11-N,N,N-trimethylammoniundecyl methacrylate chloride copolymer was prepared as follows:

Trimethylamine liquid was added from a cylinder to methanol with cooling to generate a 23.2% w/w solution. A proportion of this solution (2,073 L, 6.20 moles) was diluted with methanol (8.9 L) and a suspension of the 11-bromoundecyl methacrylate copolymer in methanol (1,882 kg @ 47.0%, 2.77 moles) was added. The mixture was stirred at ambient temperature for 1 hour, then heated to 40° and maintained between 40° and 45° for 28 hours.

The mixture was filtered on a Buchner funnel, and the filtrate was washed by stirring for 1 hour with methanol (8.9 L). The product was filtered on a Buchner funnel, and re-washed by stirring for 1 hour with methanol (8.9 L).

Concentrated hydrochloric acid (0.72 L) was added slowly to methanol (7.2 L), and the filtrate added with stirring. The mixture was stirred for 75 minutes, and the solid filtered off on a Buchner funnel. The solid was treated in an identical fashion a further four times (total of five washes).

The resultant solid was added with stirring to methanol (8.75 L). The mixture was stirred for 1 hour; the solid was filtered off on a Buchner funnel and re-washed by stirring with methanol (8.75 L) for 1 hour.

The resultant solid was added with stirring to demineralised water (14 L). The mixture was stirred for 1 hour; the solid was filtered off on a Buchner funnel and re-washed by stirring with demineralised water (14 L) for 1 hour.

The wet product (4.982 kg) was dried in the vacuum tray drier at 50° C./50 mm Hg for 100 hours to give 0.60 kg of 11-N,N,N-trimethylammoniounedecylmethacrylate copolymer (67.8% of theory).

EXAMPLE 2

The 1.6 molar % cross-linked 11-bromoundecyl methacrylate polymer (4.05 g) prepared in Example 1(b) was suspended in dimethylformamide (50 ml), N,N-dimethyloctylamine (10 ml) added, and the mixture stirred at 60° for 16 hours. The polymer was filtered and washed with dimethylformamide and methanol. Anion-exchange was accomplished by stirring the polymer in 2M HCl (300 ml) for 16 hours. It was then filtered and washed with 2M HCl, water, methanol, and ether, and finally dried under vacuum to give cross-linked 11-N,N-dimethyl-N-octyl-ammoniounedecyl methacrylate chloride co-polymer as polymer beads (4.83 g), (exchange capacity=2.26 meq $Cl^-/g$).

EXAMPLE 3

1.6 molar % cross-linked 11-bromoundecyl methacrylate co-polymer (4.72 g) prepared in Example 1b was suspended in pyridine (50 ml) and the mixture stirred at 80° for 24 hours. The polymer was filtered and washed with methanol. It was then stirred in 2M hydrochloric acid (500 ml) for 16 hours and refiltered. Washing was continued with 2M hydrochloric acid, water, methanol and ether and finally the product was dried under high vacuum to give cross-linked 11-(1-pyridinio) undecyl methacrylate chloride co-polymer beads (4.61 g), (exchange capacity=2.76 meq $Cl^-/g$).

EXAMPLES 4–5

N,N-Dimethyldodecylamine and N,N-dimethylbenzylamine were each reacted with a 1.6 molar % cross-linked 11-bromoundecyl methacrylate co-polymer (3.1 meq Br/g) (Example 1b) in dimethylformamide at 60° to give, after work up as described in Example 2, a cross-linked N,N-Dimethyl-N-dodecylammoniounedecyl methacrylate chloride co-polymer (Example 4), (exchange capacity=1.98 meq $Cl^-/g$), and a cross-linked N,N-dimethyl-N-benzylammoniounedecyl methacrylate chloride co-polymer (Example 5), (exchange capacity=2.27 meq $Cl^-/g$).

EXAMPLES 6–10

11-Bromoundecyl methacrylate (49 g) and ethylene glycol bismethacrylate (1 g) were copolymerised as in Example 1 to give, after washing, approximately 3.1 molar cross-linked 11-bromoundecylmethacrylate chloride copolymer as polymer beads (29.2 g), containing 3.0 meq Br/g.

Trimethylamine, as in Example 1c, N,N-dimethyloctylamine, N,N-dimethyl-dodecylamine, and N,N-dimethylbenzylamine, as in Example 2, and pyridine, as in Example 3, were each reacted with the above approximately 3.1 molar % cross-linked polymer to give the corresponding 11-substituted methacrylate chloride co-polymers with the following exchange capacities:

Example 6, trimethylammonio, 2.93 meq $Cl^-/g$;
Example 7, N,N-dimethyl-N-octylammonio, 2.25 meq $Cl^-$;
Example 8, N,N-dimethyl-N-dodecylammonio, 1.98 meq $Cl^-/g$;
Example 9, N,N-dimethyl-N-benzylammonio, 2.25 meq $Cl^-/g$;
Example 10, 1-pyridinio, 2.75 meq $Cl^-/g$.

EXAMPLES 11–15

11-Bromoundecyl methacrylate (49.75 g) and ethylene glycol bismethacrylate (0.25 g) were copolymerised as in Example 1 to give, after washing, approximately 0.8 molar cross-linked 11-bromoundecyl methacrylate co-polymer as polymer beads (22.8 g), containing 3.1 meq Br/g.

Trimethylamine, as in Example 1c, N,N-dimethyloctylamine, N,N-dimethyldodecylamine, and N,N-dimethylbenzylamine, as in Example 2, and pyridine, as in Example 3, were each reacted with the above polymer to give the corresponding 1-substituted undecylmethacrylate chloride co-polymers with the following exchange capacities:

Example 11, trimethylammonio, 2.76 meq $Cl^-/g$;
Example 12, N,N-dimethyl-N-octylammonio, 2.26 meq $Cl^-/g$;
Example 13, N,N-dimethyl-N-dodecylammonio, 1.99 meq $Cl^-/g$;
Example 14, N,N-dimethyl-N-benzylammonio, 2.28 meq $Cl^-/g$;
Example 15, 1-pyridinium, 2.78 meq $Cl^-/g$.

EXAMPLES 16–18

6-Chlorohexyl methacrylate (41.5 g) was prepared, as in Example 1a, from 6-chlorohexanol (50 g) and methacrylic anhydride (56.4 g). 6-Chlorohexyl methacrylate copolymer beads 4.1 meq Cl/g and containing approximately 5%, 2% and 1% w/w ( approximately 4.9, 1.9, 0.9 molar % respectively) ethylene glycol bismethacrylate as crosslinking agent were prepared by polymerising 6-chlorohexyl methacrylate, ethyl methacrylate, and ethylene glycol bismethacrylate as in Example 1b. These polymers were then sieved and either the 53–106 μm fraction for the 4.9 molar % cross-linked resin or 206–121 μm fraction for the approximately 1.9 and 0.9 molar % cross-linked resins used further. These polymers were reacted with trimethylamine as in Example 1c, to give cross-linked 6-trimethylammoniohexyl methacrylate co-polymers with the following exchange capacities:

Example 16, 4.9 molar % cross-linked, 3.16 meq $Cl^-/g$;
Example 17, 1.9 molar % cross-linked, 2.71 meq $Cl^-/g$;
Example 18, 0.9 molar % cross-linked, 2.72 meq $Cl^-/g$.

EXAMPLE 19

(a) 3-Bromopropanol (200 g), methacrylic anhydride (222 g), pyridine (134 ml) were combined with dimethylaminopyridine (4 g) with cooling to 10° in an ice bath. The reaction was stirred at room temperature for 48 hours. Water (1000 ml) was added and the aqueous solution was then acidified with dilute hydrochloric acid, and extracted with hexane (3×500 ml). The combined organic extracts were washed with 2NHCl (500 ml), water (500 ml), saturated sodium hydrogen carbonate solution (2×750 ml), water (500 ml). After drying over anhydrous magnesium sulphate, the solution was concentrated in vacuo. The resulting oil was purified by distillation to give a colourless oil, bp 66°-72°, 0.5 Torr (110 g). This oil was further purified by chromatography on silica gel with hexane:dichloromethane (50:50) as eluent, to give 3-bromopropylmethacrylate (94.3 g, 32%).

(b) 3-Bromopropyl methacrylate (41.41 g), ethylene glycol bismethacrylate (0.5 g), ethyl methacrylate (8.09 g) and azobisisobutyronitrile (AIBN) (0.5 g) were mixed and added to a solution of poly(vinylalcohol) (m.w. 125,000) (1 g) in distilled water (500 ml). The mixture was then stirred at 80° under an atmosphere of nitrogen, at such a rate as to maintain the monomers in suspension. After 7 hours the mixture was poured into distilled water. The resin formed was washed by decantation with cold and hot water, filtered and washed with water, acetone and ether. Drying under reduced pressure gives an approximately 1% (w/w) (approximately 0.9 molar %) cross-linked 3-bromopropyl methacrylate co-polymer containing 4 meq Br/g (26.9 g, 53–106 μm after sieving).

(c) The above approximately 0.9 molar % cross-linked 3-bromopropyl methacrylate co-polymer (5 g) was suspended in dimethylformamide (100 ml), N,N-dimethyloctylamine (7.5 g) was added and the mixture stirred at 70° for 20 hours. The polymer was filtered and washed in a method analogous to Example 1c to give, after drying, a cross-linked 3-(N,N-dimethyl-N-octylammonio)propyl methacrylate chloride co-polymer (4.12 g) (exchange capacity 2.64 meq Cl−/g).

EXAMPLE 20

The approximately 0.9 molar % cross-linked 3-bromopropyl polymethacrylate resin (4 g) prepared in Example 19b was suspended in dimethylformamide (100 ml), N,N-dimethyldodecylamine (10.2 g) was added and the mixture stirred at 70° for 20 hours. The polymer was filtered and washed in a method analogous to Example 1c to give, after drying, a cross-linked 3-(N,N-dimethyl-N-dodecylammonio)propyl methacrylate chloride co-polymer (5.38 g) (exchange capacity 2.36 meq Cl−/g).

EXAMPLES 21–22

3-Bromopropylmethacrylate (49.5 g) and ethylene glycol bismethacrylate (0.5 g) were polymerised as in Example 19b to give approximately 1% (w/w) (≅1.05 molar cross-linked 3-bromopropyl methacrylate co-polymer beads containing 4.7 meq Br/g (35.9 g, 53–106μ after sieving).

N,N-dimethyloctylamine, as in Example 19, N,N-dimethyldodecylamine and as in Example 20 were each reacted with the above polymer to give the corresponding cross-linked 3-substituted propylmethacrylate chloride co-polymers with the following exchange capacities:

Example 21, N,N-dimethyl-N-octylammonio, 2.95 meq Cl−/g;

Example 22, N,N-dimethyl-N-dodecylammonio, 2.57 meq Cl−/g.

EXAMPLES 23–24

3-Bromopropylmethacrylate (41.41 g), ethylene glycol bismethacrylate (1 g), hexylmethacrylate (7.59 g) azobisisobutyronitrile (0.5 g) were polymerised as in Example 19b to give an approximately 2% w/w (≅2.0 molar %) cross-linked 3-bromopropyl polymethacrylate resin containing 3.97 meq Cl/g (27 g, 53–105 μm after sieving).

N,N-dimethyloctylamine, as in Example 19, and N,N-dimethyldodecylamine, as in Example 20, were each reacted with the above polymer to give the corresponding 3-substituted propylmethacrylate chloride co-polymers with the following exchange capacities:

Example 23, N,N-dimethyl-N-octylammonio, 2.67 meq Cl−/g;

Example 24, N,N-dimethyl-N-docecylammonio, 2.39 meq Cl−/g.

EXAMPLES 25–27

3-Bromopropylmethacrylate (41.41 g), ethylene glycol bismethacrylate (1 g), laurylmethacrylate (7.5 g) and azobisisobutyronitrile (0.5 g), were polymerised as in Example 19b to give an approximately 2% w/w (≅2.1 molar %) cross-linked 3-bromopropyl methacrylate co-polymer beads containing 3.86 meq Br/g (21.2 g, 53–106μ after sieving).

Trimethylamine, as in Example 19c, N,N-dimethyloctylamine, as in Example 19, and N,N-dimethyldodecylamine, as in Example 20, were each reacted with the above polymer to give the corresponding 3-substituted propylmethacryliate chloride co-polymers with the following exchange capacities:

Example 25, trimethylammonio, 3.66 meq Cl−/g;

Example 26, N,N-dimethyl-N-octylammonio, 2.63 meq Cl−/g;

Example 27, N,N-dimethyl-N-dodecylammonio, 2.38 meq Cl−/g.

EXAMPLES 28–30

11-Bromoundecyl methacrylate co-polymer beads containing 3.1 meq Br/g and containing approximately 2%, 1% and 0.5% w/w (≅ approximately 2.5, 1.25 and 0.64 molar %) 1,6-hexanediol bismethacrylate as cross-linking agent were prepared by polymerising 11-bromoundecyl methacrylae and 1,6-hexanediol bismethacrylate as in Example 1b. These polymers were reacted with trimethylamine as in Example 1c to give cross-linked 11-trimethylammonioundecylmethacrylate co-polymers with the following exchange capacities:

Example 28, 2.5 molar % cross-linked, 2.82 meq Cl−/g;

Example 29, 1.25 molar % cross-linked, 2.85 meq Cl−/g;

Example 30, 0.54 molar % cross-linked, 2.88 meq Cl−/g.

EXAMPLES 31–33

11-Bromoundecyl methacrylate co-polymer beads containing 3.0–3.1 meq Br/g and containing 2%, 1% and 0.5% w/w (≅4.8, 2.4, 1.2 molar %) divinyl benzene as cross-linking agent were prepared by polymerising 11-bromoundecyl methacrylate and divinyl benzene as in Example 1b. These polymers were reacted with trimethylamine as in Example 1c to give cross-linked 11-trimethylammonioundecylmethacrylate co-polymers with the following exchange capacities:

Example 31, 4.8 molar % cross-linked, 2.77 meq Cl−/g;

Example 32, 2.4 molar % cross-linked, 2.81 meq Cl−/g;

Example 33, 1.2 molar % cross-linked, 2.86 meq Cl$^-$/g.

EXAMPLES 34–36

11-Bromoundecyl methacrylate co-polymer beads containing approximately 3.0–3.1 meq Br/g and containing approximately 4%, 1.6% and 0.8% w/w ($\cong$3.9, 1.5, 0.8 molar %) tetraethylene glycol bismethacrylate as cross-linking agent were prepared by polymerising 11-bromoundecyl methacrylate and tetraethylene glycol bismethacrylate as in Example 1b. These polymers were reacted with trimethylamine as in Example 1c to give cross-linked 11-trimethylammoniundecyl methacrylate co-polymers with the following exchange capacities:

Example 34, 3.9 molar % cross-linked, 2.75 meq Cl$^-$/g;
Example 35, 1.5 molar % cross-linked, 2.83 meq Cl$^-$/g;
Example 36, 0.8 molar % cross-linked, 2.87 meq Cl$^-$/g.

EXAMPLES 37–39

11-Bromoundecyl methacrylate co-polymer beads containing approximately 3.1 meq Br/g and containing 2%, 1% and 0.5% w/w ($\cong$1.9, 1.0, 0.5 molar %) 2-ethyl-2-(hydroxymethyl)-1,3-propanediol trismethacrylate as cross-linking agent were prepared by polymerising 11-bromoundecyl methacrylate and 2-ethyl-2-(hydroxymethyl)-1,3-propanediol trismethacrylate as in Example 1b. These polymers were reacted with trimethylamine as in Example 1c to give cross-linked 11-trimethylammoniundecyl methacrylate co-polymers 2-ethyl-2-(hydroxymethyl)-1,3-propanediol trismethacrylate as cross-linking agent were prepared by polymerising 11-bromoundecyl methacrylate and 2-ethyl-2-(hydroxymethyl)-1,3-propanediol trismethacrylate as in Example 1b. These polymers were reacted with trimethylamine as in Example 1c to give cross-linked 11-trimethylammoniundecyl methacrylate co-polymers with the following exchange capacities:

Example 37, 1.9 molar % cross-linked 2.85 meq Cl$^-$/g;
Example 38, 1.0 molar % cross-linked, 2.83 meq Cl$^-$/g;
Example 39, 0.5 molar % cross-linked, 2.91 meq Cl$^-$/g.

EXAMPLES 40–42

10-Bromodecanol (340 g) and methacrylic anhydride (200 g) were reacted as described in Example 1a to give 10-bromodecylmethacrylate (193 g) after chromatography in silica gel.

10-Bromodecylmethacrylate (49 g) and ethylene glycol bismethacrylate (1 g) were co-polymerised as for Example 1c to give approximately 2% w/w ($\cong$3.0 molar %) cross-linked 10-bromodecyl methacrylate co-polymer beads (46.5 g).

Portions of the above cross-linked polymer were separately reacted with trimethylamine, dimethyldodecylamine and pyridine as described in Examples 1, 4 and 3 to give after washing the corresponding cross-linked 10-substituted-decylmethacrylate chloride co-polymers with the following exchange capacities:

Example 40, trimethylammonio, 3.1 meq Cl$^-$/g;
Example 41, N,N-dimethyl-N-dodecylammonio, 2.1 meq Cl$^-$/g,
Example 42, 1-pyridinio, 2.9 meq Cl$^-$/g.

EXAMPLES 43–44

10-Bromodecylmethacrylate (49.5 g) and ethylene glycol bismethacrylate (0.5 g) were co-polymerised as for Example 1c to give approximately 1% w/w ($\cong$1.5 molar %) cross-linked 10-bromodecylmethacrylate co-polymer beads (42 g).

Portions of the above cross-linked polymer were separately reacted with trimethylamine and N,N-dimethyldodecylamine as in Examples 1 and 4 to give, after washing, the corresponding cross-linked 10-substituted decylmethacrylate co-polymers with the following exchange capacities:

Example 43, trimethylammonio, 3.0 meq Cl$^-$/g;
Example 44, N,N-dimethyl-N-dodecylammonio, 2.1 meq Cl$^-$/g.

EXAMPLES 45–47

12-Bromododecanol (340 g) and methacrylic anhydride (200 g) were reacted as described in Example 1a to give 12-bromododecylmethacrylate (270 g) after chromatography on silica gel.

12-Bromododecylmethacrylate (46 g) and ethylene glycol bismethacrylate (0.92 g) were co-polymerised as for Example 1c to give approximately 2% w/w ($\cong$3.2 molar %) cross-linked 12-bromododecylmethacrylate co-polymer beads (44.8 g).

Portions of the above cross-linked polymer were separately reacted with trimethylamine, N,N-dimethyldodecylamine, and pyridine as described in Examples 1,4 and 3 to give, after washing, the corresponding cross-linked 12-substituted-decyl methacrylate chloride co-polymers with the following exchange capacities:

Example 45, trimethylammonio, 2.9 meq Cl$^-$/g;
Example 46, N,N-dimethyl-N-dodecylammonio, 2.0 meq Cl$^-$/g;
Example 47, 1-pyridinio, 3.0 meq Cl$^-$/g.

EXAMPLE 48

4.51 g of the 1.6 molar % cross-linked 11-bromoundecyl methacrylate co-polymer prepared in Example 1b was reacted with N-methylimidazole (10 g) in dimethylformamide (40 ml) to give, after washing as in Example 1c, the corresponding 11-(N-(N'-methylimidazolio)undecyl methacrylate chloride co-polymer (4.12 g) (exchange capacity=2.64 meq Cl$^-$/g).

EXAMPLE 49

4.2 g of the 1.6 molar % cross-linked 11-bromoundecyl methacrylate co-polymer prepared in Example 1b was reacted with N-methylmorpholine (9.2 g) in dimethylformamide (40 ml) to give, after washing as in Example 1c, the corresponding 11-(N-methylmorpholinio)undecyl methacrylate chloride co-polymer (4.0 g) (exchange capacity=2.34 meq Cl$^-$/g).

EXAMPLE 50

4.75 g of the 1.6 molar % cross-linked 11-bromoundecyl methacrylate co-polymer prepared in Example 1b was reacted with N-methylpiperidine (8.2 g) in dimethylformamide (40 ml) to give, after washing as in Example 1c, the corresponding 11- (N-methylpiperidinio) undecyl methacrylate chloride co-polymer (4.46 g), (exchange capacity=2.49 meq Cl$^-$/g).

EXAMPLE 51

(a) Anhydrous dimethyl sulphoxide (64 ml) was added to a solution of oxalyl chloride (52 ml) in dichloromethane (1200 ml) at −60°. After 20 minutes, 11-bromoundecanol (101.2 g) in dichloromethane (400 ml) was added to the reaction mixture. After a further 1 hour, triethylamine (280 ml) was added slowly and 10 minutes after the completion of the addition the reaction mixture was allowed to come to room temperature. The organic phase was washed with water (500 ml), 2M HCl (2×500 ml), and saturated sodium hydrogen carbonate solution (2×500 ml), dried (MgSO$_4$), and concentrated in vacuo. The resulting oil was distilled under reduced pressure to yield 11-bromoundecanol (b.p. 117–119°, 0.15mmHg) (80.7 g, 81% yield).

(b) A solution of (6-hydroxyhexyl)triphenylphosphonium bromide (5.0 g) in dichloromethane (20 ml) was added dropwise to a mixture of potassium tertiary-butoxide (2.8 g) in tetrahydrofuran (100 ml) at 5°. After ten minutes, 11-bromoundecanol (2.8 g) in tetrahydrofuran (20 ml) was added and the reaction stirred at 5° until TLC indicated completion of the reaction. Water (20 ml) was added and the mixture then concentrated in vacuo. Water (20 ml) was added to the residue and the aqueous phase extracted with ether (2×50 ml). The combined organic extracts were dried (MgSO$_4$) and concentrated in vacuo to give a brown oil. This was subjected to column chromatography to yield 17-bromoheptadec-6-en-1-ol (1.7 g, 45%).

(c) 17-Bromoheptadec-6-en-l-ol (33.8 g) was subjected to hydrogenation in a Paar hydrogenation apparatus (50 psi initial hydrogen pressure), using ethanol as solvent and 10% palladium on charcoal as catalyst, to yield 17-bromoheptadecan-1-ol (26.1 g, 76% yield).

(d) 17-Bromoheptadecyl methacrylate (14.6 g, 48% yield) was prepared, as in Example 1a, from 17-bromoheptadecan-1-ol (25 g) and methacrylic anhydride (11.1 ml).

(e) A 17-bromoheptadecyl methacrylate polymer (5.3 g) containing 2.5 meq Br/g and 2 molar % ethylene glycol bismethacrylate as cross-linking agent was prepared by polymerising 17-bromoheptadecyl methacrylate (13.25 g) and ethylene glycol bismethacrylate (0.13 g) as in Example 1b.

(f) The above 2 molar % cross-linked 17-bromoheptadecyl methacrylate polymer (5.2 g) was reacted with trimethylamine, as in Example 1c, to give a 17-N,N,N-trimethylammonioheptadecyl methacrylate chloride co-polymer (4.65 g) (exchange capacity=2.35 meq Cl$^-$/g).

EXAMPLES 52–53

3-Bromopropyl methacrylate (Example 19a) (41.41 g), ethylene glycol bismethacrylate (0.5 g), lauryl methacrylate (8.09 g) and azobisisobutyronitrile (0.5 g), were polymerised as in Example 19b to give approximately 1% w/w (≅1.26 molar %) cross-linked 3-bromopropyl methacrylate co-polymer beads containing 3.74 meq Br/g (24.34 g, 53–106μ after sieving).

N,N-dimethyloctylamine, as in Example 19, and N,N-dimethyldodecylamine, as in Example 20, were each reacted with the above polymer to give the corresponding 3-substituted propylmethacrylate chloride co-polymers with the following exchange capacities:

Example 52, N,N-dimethyl-N-octylammonio, 2.33 meq Cl$^-$/g;

Example 53, N,N-dimethyl-N-dodecylammonio, 2.14 meq Cl$^-$/g.

EXAMPLES 54–55

3-Bromopropyl methacrylate (41.41 g), ethylene glycol bismethacrylate (0.5 g), styrene (8.09 g) and azobisisobutyronitrile (0.5 g), were polymerised as in Example 19b to give an approximately 1% w/w (≅1.26 molar %) cross-linked 3-bromopropyl methacrylate co-polymer beads containing 3.97 meq Br/g (25.96 g, 53–106μ after sieving).

N,N-Dimethyloctylamine, as in Example 19, and N,N-dimethyldodecylamine, as in Example 20, were each reacted with the above polymer to give the corresponding 3-substituted propylmethacrylate chloride co-polymers with the following exchange capacities:

Example 54, N,N-dimethyl-N-octylammonio, 2.49 meq Cl$^-$/g;

Example 55, N,N-dimethyl-N-dodecylammonio, 2.21 meq Cl$^-$/g.

EXAMPLES 56–57

Methacrylic anhydride (236 ml) was added to a solution of 8-bromooctanol (508.9 g) in pyridine (186 ml) and hexane (1500 ml) at 10°. After 1 hour at 10°, dimethylaminopyridine (5 g) was added keeping the temperature controlled with an ice-bath. The reaction mixture was stirred for 3 days at room temperature. 2M HCl (1000 ml) was added and the hexane layer was removed. The aqueous layer was washed with hexane (500 ml). The combined organic extracts were washed with 2M HCl (2×500 ml), water (500 ml), saturated sodium hydrogen carbonate solution (2×500 ml) and finally water (1000 ml). After drying (MgSO$_4$), the solution was concentrated in vacuo to give a clear oil (572.2 g). This was chromatographed on silica gel with hexane: dichloromethane (50:50) as eluent, to give 8-bromooctyl methacrylate (230.2 g, 37%).

8-Bromopropyl methacrylate (49.5 g), ethylene glycol bismethacrylate (0.5 g) and azobisisobutyronitrile (0.5 g), were polymerised as in Example 19b to give an approximately 1% w/w (≅1.48 molar %) cross-linked 3-bromooctyl methacrylate co-polymer beads containing 3.53 meq Br/g (41.66 g).

Trimethylamine, as in Example 1c, N,N-dimethyldodecylamine, as in Example 20, were each reacted with the above polymer to give the corresponding 8-substituted octylmethacrylate chloride co-polymers with the following exchange capacities:

Example 56, trimethylammonio, 3.15 meq Cl$^-$/g;

Example 57, N,N-dimethyl-N-dodecylammonio, 2.02 meq Cl$^-$/g.

EXAMPLE 58

6-Chlorohexyl methacrylate ethylene glycol bismethacrylate co-polymer (4.1 meq Cl/g, approximately 1.9 molar % cross-linking) (c.f. Example 17) (14.1 g) was reacted with sodium bromide (6 g) and ethyl bromide (63.2 g) in N-methylpyrrolidone (200 ml) at 65° for 6 days. The slurry was then sieved and the fraction <53 μM discarded. The remaining polymer was washed with water, methanol, acetone and diethylether and dried under vacuum for 16 hours to give 6-bromohexyl methacrylate ethylene glycol bismethacrylate co-polymer (14.97 g, 3.47 meq Br/g, no Cl detected).

The above polymer (4 g) was reacted with N,N-dimethyloctylamine (7.6 g) in dimethylformamide (40 ml) at 70° for 16 hours. The mixture was then cooled and sieved and the fraction <53 μM discarded. The remaining polymer was washed with methanol, aqueous 2N hydrochloric acid, water, methanol and diethyl ether, dried under vacuum to give the corresponding 6-N,N-dimethyl-N-octylammoniohexyl methacrylate chloride ethylene glycol bismethacrylate co-polymer as off-white polymer beads (4.72 g, 2.42 meq Cl−/g).

EXAMPLE 59

The 6-bromohexyl methacrylate co-polymer prepared in Example 58 (3.66 g) was reacted with N,N-dimethyldodecylamine (7.75 g) in dimethylformamide (40 ml) as for Example 58 and after similar work-up gave approximately 1.9 molar cross-linked N,N-dimethyl-N-dodecylammonio hexyl methacrylate chloride ethylene glycol bismethacrylate co-polymer as off-white polymer beads (5.01 g, 2.1 meq Cl−/g).

EXAMPLE 60

6-Chlorohexyl methacrylate ethylene glycol bismethacrylate co-polymer (4.1 meq Cl/g, approximately 0.9 molar % cross-linking) (c.f. Example 17) (7.30 g) was reacted with sodium bromide (3.1 g) and ethyl bromide (32.7 g) in N-methylpyrrolidone (200 ml) at 65° for 6 days. The slurry was then sieved and the fraction <53 μM discarded. The remaining polymer was washed with water, methanol, acetone and diethylether and dried under vacuum for 16 hours to give 6-bromohexyl methacrylate ethylene glycol bismethacrylate co-polymer (6.82 g, 3.4 meq Br/g, no Cl detected).

The above polymer (3.4 g) was reacted with N,N-dimethyloctylamine (7.6 g) in dimethylformamide (40 ml) at 70° for 16 hours. The mixture was then cooled and sieved and the fraction <53 μM discarded. The remaining polymer was washed with methanol, aqueous 2N hydrochloric acid, water, methanol and diethyl ether, dried under vacuum to give the corresponding 6-N,N-dimethyl-N-octylammoniohexyl methacrylate chloride ethylene glycol bismethacrylate co-polymer as off-white polymer beads (3.47 g, 2.45 meq Cl−/g).

EXAMPLE 61

The 6-bromohexyl methacrylate co-polymer prepared in Example 60 (3.28 g) was reacted with N,N-dimethyldodecylamine (7.75 g) in dimethylformamide (40 ml) as for Example 58 and after similar work-up gave approximately 0.9 molar % cross-linked N,N-dimethyl-N-dodecylammonio hexyl methacrylate chloride ethylene glycol bismethacrylate co-polymer as off-white polymer beads (4.37 g, 2.14 meq Cl−/g).

EXAMPLE 62

10-Bromodecyl methacrylate (47.75 g) and ethylene glycol bismethacrylate (0.25 g) were polymerised as described in Example 19c to give a co-polymer (41.5 g) containing 3.2 meq Br/g and approximately 0.5% w/w (0.8 molar %) cross-linked. This polymer (7.78 g) was treated with 33% alcoholic trimethylamine (50 ml) in DMF (170 ml) as described for Example 1c to give, after similar work up, approximately 0.8 molar % cross-linked 10-trimethylammoniodecyl methacrylate chloride ethylene glycol bismethacrylate co-polymer as off-white beads (6.42 g, 3.1 meq Cl−/g).

EXAMPLE 63

11-Bromoundecyl methacrylate tetraethylene glycol bismethacrylate co-polymer (3.1 meq Br/g, approximately 1.5 molar % cross-linking, c.f. Example 34) was reacted with N,N-dimethyloctylamine as in Example 2 to give 11-(N,N-dimethyl-N-octylammonioundecyl) methacrylate chloride tetraethylene glycol bismethacrylate co-polymer as off-white beads (2.25 meq Cl−/g).

EXAMPLE 64

11-Bromoundecyl methacrylate tetraethylene glycol bismethacrylate co-polymer (3.1 meq Br/g, approximately 0.8 molar % cross-linked c.f. Example 35) was reacted with N,N-dimethyloctylamine as in Example 2 to give 11-(N,N-dimethyl-N-octylammonioundecyl) methacrylate chloride tetraethylene glycol bismethacrylate co-polymer as off-white beads (2.25 meq Cl−/g).

EXAMPLE 65

12-Bromododecyl methacrylate (49.5 g) and ethylene glycol bismethacrylate (0.5 g) were co-polymerised as for Example 1c to give approximately 1% w/w (≅1.6 molar %) cross-linked 12-bromododecyl methacrylate co-polymer beads (38.8 g). This polymer was reacted with trimethylamine as described in Example 1 to give 12-trimethylammoniododecyl methacrylate chloride ethylene glycol bismethacrylate co-polymer beads (2.78 meq Cl−/g, approximately 1.6 molar % cross-linked).

EXAMPLE 66

12-Bromododecyl methacrylate (49.75 g) and ethylene glycol bismethacrylate (0.25 g) were co-polymerised as for Example 1c to give approximately 0.5% w/w (≅0.8 molar %) cross-linked 12-bromododecyl methacrylate co-polymer beads (20 g). This polymer was reacted with trimethylamine as described in Example 1 to give 12-trimethylammoniododecyl methacrylate chloride ethylene glycol bismethacrylate co-polymer beads (2.74 meq Cl−/g, approximately 0.8 molar % cross-linked).

Example A

A chewable tablet composition can be prepared from the following:

|  | mg/tablet |
| --- | --- |
| Compound of Example 6: | 1250 |
| Silicon dioxide | 15 |
| Microcrystalline cellulose | 280 |
| Sorbitol | 445 |
| Lactose | 450 |
| Sweetener | 5 |
| Peppermint | 30 |
| Magnesium Stearate | 25 |
|  | 2500 mg |

Example B

A food additive composition, for example, a sachet for reconstitution or mixing with food, is prepared by incorporating into a powder formulation compound of Example 6 (250 mg), sodium carboxymethylcellulose (50 mg), sucrose (2400 mg) and flavours (50 mg).

DATA

In vitro Dissociation assay

The following assay provides a measure of affinity of the polymers of the invention for the bile acid, glycocholrate (GC) based on the amount of GC bound at a subsaturating concentration of 5 mM (t=0), and an estimate of the rate at which this bile acid dissociates into a large volume of buffer. The results are obtained as initial amounts of GC bound (t=0) and amounts remaining bound after 2 minutes in buffer (t=2min); from these figures the % dissociation i.e. the proportion of bound GC dissociated from the polymer after 2 minutes can be obtained. The lower the % dissociation the more efficient the polymer can be expected to be in extracting bile acids in vivo.

Method

Test compound (150 mg) was equilibrated with 5 mM sodium glycocholate (30 ml) in Krebs' buffer. The compound was separated by centrifugation and the total bound determined by subtraction of the amount in the supernatant from the total bile acid used. Dissociation was measured by resuspending the compound in Krebs' buffer, shaking and sampling the mixture through a filter at several time points up to 20 minutes. Radioactivity and hence bile acid dissociated was determined in the filtrate.

Results

The following % dissociation figures were obtained:

| Examples | % Dissociation (range) |
|---|---|
| 1 to 15, 17, 20 to 24 27 to 51, 58 to 65 | 4 to 15 |
| 16, 18, 19, 25, 26 and 54 to 58 | 16 to 36 |

As the results demonstrate, the claimed series of compounds represent a series of polymers having a high capacity for binding bile acids at equilibrium. This capacity is particularly apparent when the compounds of the invention are compared with related acrylic polymers in which, for example n is 1 to 5 and $R^1$ to $R^3$ are all $C_{1-4}$alkyl (cf: U.S. Pat. No. 3,787,474).

To illustrate this, two 3-trimethylamminiopropyl methacrylate chloride copolymer (examples A and B prepared according to the procedures analogous to those hereinbefore described) were tested in the same assay and compared to the closest analogues of the claimed invention. The results are summarised in Table 1, in which EGBMA is ethylene glycol bis-methacrylate, and EMA is ethyl methacrylate.

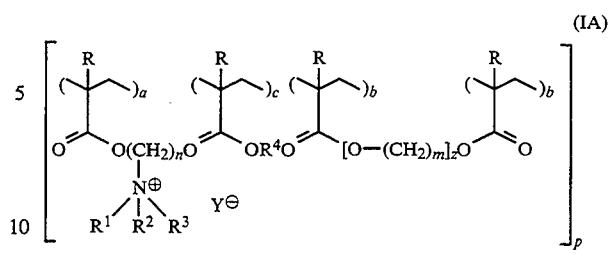

(IA)

in which (a), (b) and (c) indicate the relative molar percentages of the units present in the polymer, (a) being from about 60 to about 99.5 molar percent and (b) being from about 0.5 to about 8 molar percent;

R, is $C_{1-4}$alkyl;

$R^1$ and $R^2$ are the same or different and are each $C_{1-4}$alkyl, and $R^3$ is $C_{1-20}$alkyl or $C_{1-20}$aralkyl; or $R^1$ is $C_{1-4}$alkyl and $R^2$ and $R^3$ together with the nitrogen atom to which they are attached form a saturated ring, optionally containing one or more further heteroatoms; or $R^1$ to $R^3$ together with the nitrogen atom to which they are attached form an unsaturated ring, optionally containing one or more further heteroatoms;

n is 1 to 20; and $R^4$ is $C_{1-20}$alkyl;

m is 2 to 6;

z is 1 to 4;

$Y^-$ is a physiologically acceptable counter ion; and p is a number indicating the degree of polymerisation of said polymer; provided that, (i) when n is 1 to 5, $R^1$, $R^2$, and $R^3$ are not all $C_{1-4}$alkyl, (ii) when n is 1 to 5, $R^1$, $R^2$, and $R^3$, do not together form an unsaturated ring.

2. A polymer as claimed in claim 1 in which z is 1 and m is 2.

3. A polymer as claimed in claim 2 in which n is 10 to 12.

4. A polymer as claimed in claim 3 in which $R^1$ to $R^3$ are all $C_{1-4}$alkyl.

5. A polymer as claimed in claim 4 which is 11-N,N,N-trimethylammonioundecyl methacrylate chloride co-polymer.

TABLE 1

| Test Compound Example No. | Molar % Cross-link[1] | X | $X^1$ | n | $NR^1R^2R^3$ | % Diss'n |
|---|---|---|---|---|---|---|
| A | 1.05 | EGBMA | — | 3 | $NMe_3$ | 100 |
| 2 | 1.6 | EGBMA | — | 11 | $NMe_2Octyl$ | 12 |
| 1 | 1.6 | EGBMA | — | 11 | $NMe_3$ | 5 |
| 21 | 1.05 | EGBMA | — | 3 | $NMe_2Octyl$ | 14 |
| 22 | 1.05 | EGBMA | — | 3 | $NMe_2Dodecyl$ | 8 |
| 43 | 1.5 | EGBMA | — | 10 | $NMe_3$ | 7 |
| B | 0.7 | EGBMA | EMA | 3 | $NMe_3$ | 62 |
| 18 | 0.9 | EGBMA | EMA | 6 | $NMe_3$ | 32 |
| 19 | 0.9 | EGBMA | EMA | 3 | $NMe_2Octyl$ | 23 |
| 20 | 0.9 | EGBMA | EMA | 3 | $NMe_2Dodecyl$ | 10 |
| 60 | 0.9 | EGBMA | EMA | 6 | $NMe_2Octyl$ | 14 |
| 61 | 0.9 | EGBMA | EMA | 6 | $NMe_2Dodecyl$ | 5 |

[1]Calculated molar % cross-link based on 1% w/w of cross-link in starting halo-substituted polymer.

6. A polymer as claimed in claim 4 which is 12-N,N,N-trimethylammoniododecyl methacrylate chloride ethylene glycol bismethacrylate co-polymer.

7. A polymer as claimed in claim 1 which is 11-N,N-dimethyl-N-octyl-ammonioundecyl methacrylate chloride co-polymer.

What is claimed is:

1. A polymer of structure (IA)

8. A polymer as claimed in claim 1 which is 3-N,N-dimethyl-N-dodecyl-ammoniopropyl methacrylate chloride co-polymer.

9. A polymer as claimed in claim 1 which is 10-N,N,N-trimethylammoniodecyl methacrylate chloride co-polymer.

10. A polymer as claimed in claim 1 which is 6-N,N-dimethyl-N-dodecyl-ammoniohexyl methacrylate chloride ethylene glycol bismethacrylate co-polymer.

11. A polymer as claimed in claim 1 which is 6-N,N-dimethyl-N-octylammoniohexyl methacrylate chloride ethylene glycol bismethacrylate co-polymer.

12. A polymer as claimed in claim 1 which is 3-(N,N-dimethyl-N-dodecylammonio)propyl methacrylate chloride co-polymer.

13. A method of lowering serum cholesterol levels in mammals which comprises administering to a subject in need thereof an effective amount of a polymer of structure (I)

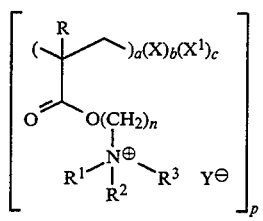

in which a, b and c indicate the relative molar percentages of the units present in the polymer, (a) being from about 25 to about 99.5 molar percent, and (b) being from about 0.5 to about 8 molar percent;

X is a cross-linking unit;

$X^1$ is a comonomer unit;

R is hydrogen or $C_{1-4}$alkyl;

$R^1$ and $R^2$ are the same or different and are each $C_{1-4}$alkyl, and $R^3$ is $C_{1-20}$alkyl or $C_{1-20}$aralkyl; or $R^1$ is $C_{1-4}$alkyl and $R^2$ and $R^3$ together with the nitrogen atom to which they are attached form a saturated ring, optionally containing one or more further heteroatoms; or $R^1$ to $R^3$ together with the nitrogen atom to which they are attached form an unsaturated ring, optionally containing one or more further heteroatoms;

n is 1 to 20;

p is a number indicating the degree of polymerisation of the polymer; and $Y^-$ is a physiologically acceptable counter ion, provided that (i) when n is 1 to 5, $R^1$, $R^2$ and $R^3$ are not all $C_{1-4}$alkyl, and (ii) when n is 1 to 5, $R^1$, $R^2$ and $R^3$ do not together form an unsaturated ring.

14. A method according to claim 13 in which the polymer of structure (I) is 11-N,N,N-trimethylammonioundecyl methacrylate chloride co-polymer.

15. A method according to claim 13 in which the polymer of structure (I) is 12-N,N,N-trimethylammonododecyl methacrylate chloride ethylene glycol bismethacrylate co-polymer.

16. A method of treatment of atherosclerosis which comprises administering to a subject in need thereof an effective amount of a polymer of structure (I)

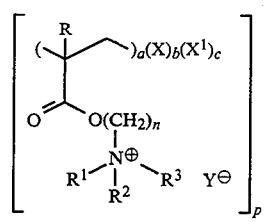

in which a, b and c indicate the relative molar percentages of the units present in the polymer, (a) being from about 25 to about 99.5 molar percent, and (b) being from about 0.5 to about 8 molar percent;

X is a cross-linking unit;

$X^1$ is a comonomer unit;

R is hydrogen or $C_{1-4}$alkyl;

$R^1$ and $R^2$ are the same or different and are each $C_{1-4}$alkyl, and $R^3$ is $C_{1-20}$alkyl or $C_{1-20}$aralkyl; or $R^1$ is $C_{1-4}$alkyl and $R^2$ and $R^3$ together with the nitrogen atom to which they are attached form a saturated ring, optionally containing one or more further heteroatoms; or $R^1$ to $R^3$ together with the nitrogen atom to which they are attached form an unsaturated ring, optionally containing one or more further heteroatoms;

n is 1 to 20;

p is a number indicating the degree of polymerisation of the polymer; and $Y^-$ is a physiologically acceptable counter ion, provided that (i) when n is 1 to 5, $R^1$, $R^2$ and $R^3$ are not all $C_{1-4}$alkyl, and (ii) when n is 1 to 5, $R^1$, $R^2$ and $R^3$ do not together form an unsaturated ring.

17. A method according to claim 16 in which the polymer of structure (I) is 11-N,N,N-trimethylammonioundecyl methacrylate chloride co-polymer.

18. A method according to claim 16 in which the polymer of structure (I) is 12-N,N,N-trimethylammonododecyl methacrylate chloride ethylene glycol bismethacrylate co-polymer.

19. A pharmaceutical composition comprising a polymer of structure I

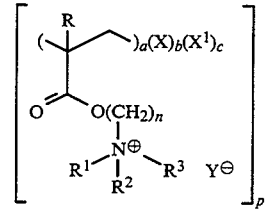

in which a, b and c indicate the relative molar percentages of the units present in the polymer, (a) being from about 25 to about 99.5 molar percent, and (b) being from about 0.5 to about 8 molar percent;

X is a cross-linking unit;

$X^1$ is a comonomer unit;

R is hydrogen or $C_{1-4}$alkyl;

$R^1$ and $R^2$ are the same or different and are each $C_{1-4}$alkyl, and $R^3$ is $C_{1-20}$alkyl or $C_{1-20}$aralkyl; or $R^1$ is $C_{1-4}$alkyl and $R^2$ and $R^3$ together with the nitrogen atom to which they are attached form a saturated ring, optionally containing one or more further heteroatoms; or $R^1$ to $R^3$ together with the nitrogen atom to which they are attached form an unsaturated ring, optionally containing one or more further heteroatoms;

n is 1 to 20;

p is a number indicating the degree of polymerisation of the polymer; and $Y^-$ is a physiologically acceptable counter ion, provided that (i) when n is 1 to 5, $R^1$, $R^2$ and $R^3$ are not all $C_{1-4}$alkyl, and (ii) when n is 1 to 5, $R^1$, $R^2$ and $R^3$ do not together form an unsaturated ring; in association with a pharmaceutically acceptable carrier.

20. A pharmaceutical composition as claimed in claim 19 in which the polymer of structure (I) is 11-N,N,N-trimethylammonioundecyl methacrylate chloride co-polymer.

21. A pharmaceutical composition as claimed in claim 19 in which the polymer of structure (I) is 12-N,N,N-trimethylammoniododecyl methacrylate chloride ethylene glycol bismethacrylate co-polymer.

* * * * *